United States Patent [19]

Kawahara

[11] Patent Number: 4,904,448
[45] Date of Patent: Feb. 27, 1990

[54] PATCH TEST MATERIALS FOR THE DETECTION OF METAL ALLERGIES

[75] Inventor: Haruyuki Kawahara, Moriguchi, Japan

[73] Assignees: G-C Dental Industrial Corp., Tokyo; Haruyuki Kawahara, both of Japan

[21] Appl. No.: 222,747

[22] Filed: Jul. 22, 1988

[30] Foreign Application Priority Data

Aug. 21, 1987 [JP] Japan .................................. 62-206534

[51] Int. Cl.$^4$ ........................ G01N 31/22; A61F 13/00
[52] U.S. Cl. .......................................... 422/56; 422/58; 436/513; 128/743; 604/304; 604/307; 424/9
[58] Field of Search ....................... 422/50, 56, 57, 58; 436/513; 128/743; 604/304, 307; 424/2, 9, 447

[56] References Cited

U.S. PATENT DOCUMENTS 3,833,722  9/1974  Graybill .............................. 424/2 X
4,125,603 11/1978  Audibert ................................ 424/88
4,530,364  7/1985  Huggins .......................... 128/743 X

FOREIGN PATENT DOCUMENTS 2909071  9/1980  Fed. Rep. of Germany ...... 128/743
8601994  4/1986  PCT Int'l Appl. ................... 128/743

Primary Examiner—Christine M. Nucker
Assistant Examiner—Rebekah A. Griffith
Attorney, Agent, or Firm—Oblon, Spivak, McClelland, Maier & Neustadt

[57] ABSTRACT

A patch test material for the detection of metal allergies which contains a dental metal, noble or base, with which an allergic reaction aid such as a biological high molecular weight compound, e.g., a protein is present.

5 Claims, 1 Drawing Sheet

FIG. 1
FIG. 2
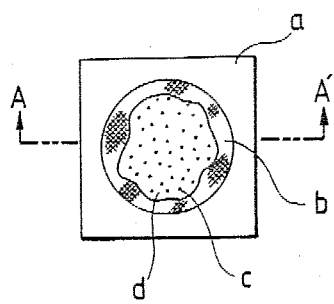
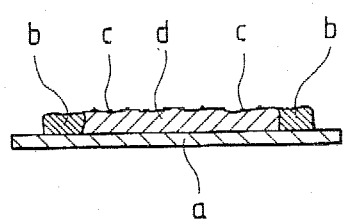
FIG. 3
FIG. 4
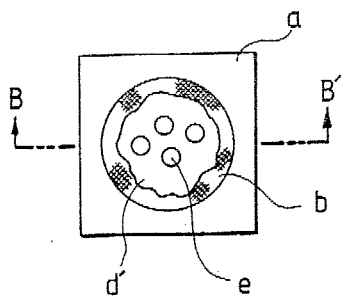
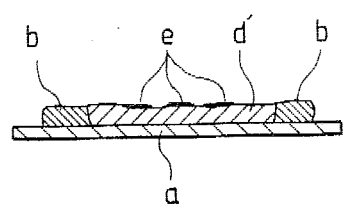
FIG. 5
FIG. 6
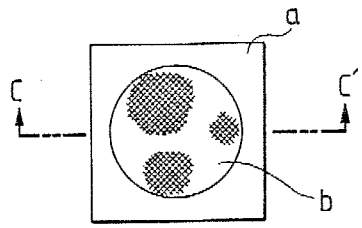
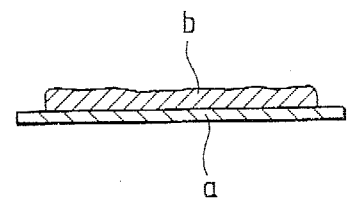

PATCH TEST MATERIALS FOR THE DETECTION OF METAL ALLERGIES

BACKGROUND OF THE INVENTION

1. Field of the Invention

The present invention relates to a patch test material for the detection of metal allergies in dentistry, which is used to make simple and highly accurate determinations of whether or not metal allergies are developed in the presence of a dental metal (a pure metal or a metal alloy) to be topically applied with an allergic reaction aid.

2. Statement of the Prior Art

Metal allergies refer to an allergic phenomenon caused by a metal, which is an incomplete antigen (called hapten) that becomes an antigen only when the metal bonds to tissue proteins. In other words, upon directly contacting the skin, a certain metal has a primary influence upon the structure of a cell and the process of an enzymatic reaction, thus causing contact dermatitises. Included further in allergic diseases developed as antigen-antibody reactions are skin ulcers, stomatitis, conjunctivitis, sensitive pneumonia, bronchial asthma, pneumonic fibrosis and so on.

Metals included in dental metallic materials and responsible for metal allergies are not only base metal elements such as Be, Ni, Co, Fe and Cr but also noble metal elements such as Au, Pt, Ag, Cu and Hg. Referring in detail to the metal allergies as mentioned above, a metal is present in the form of three phases, i.e., a metallic vapor, a metal salt and a pure metal or a metal alloy.

Not only metal allergies but also cancers or acute toxicoses are caused by metallic vapors emanating from metal melts. It is also well-known that metal allergies due to salts of metals used in plating, coating and leather tanning fields such as, for instance, nickel, cobalt and chromium, appear as chronic dermatitises and asthmatic diseases.

Unlike a pure metal or a metal alloy, a metal salt undergoes easy ionization and becomes a metal hapten upon contacting the skin or the mucous membranes of the respiratory organs. The metal hapten then bonds especially to proteins in tissue fluids, giving an organo-metallic compound which in turn becomes an antigen so sensitive to an individual as to produce an antibody. If the antigen re-enters the individual, then metal allergic reactions appear as antigenantibody reactions. It is understood that metal allergies are developed through the following three barriers:

(1) A metal is ionized.

(2) Antigenicity cannot be acquired until the thus ionized metal bonds to a high molecule in tissue fluids and becomes an organometallic compound.

(3) An antigen-antibody reaction appears only after the antigen re-enters an individual.

Metal allergies cannot be fully developed until the above three barriers are passed through.

Heretofore, the development of contact dermatitises due to metal allergies as mentioned above has generally been examined by the following patch test. As an example, the determination of metal allergies due to Ni is made as follows:

Metallic Ni is dissolved in an electrolyte into Ni-$SO_4.6H_2O$, which is then regulated to a concentration of $2\times 10^{-1}$ moles/liter with distilled water. The resulting solution is added dropwise onto gauze, which is afterwards applied thereon with a patch test plaster. After allowed to stand for 48 hours, the patch testing plaster is removed. After the lapse of further 24 hours, reaction sites are observed to estimate inflammations on them. The estimation of the reactions has been made in terms of the magnitude of positive reactions in comparison with controls comprising a plaster alone. To sum up, the reactions to metal allergies are generally examined by a method comprising the steps of, firstly, dissolving the metal for its ionization to form a metal salt solution; secondly, impregnating one or three droplets of that solution into gauze; and finally, applying a sealable patch test plaster thereon. In some cases, use may be made of first-aid plasters such as Kizu-Pad or a band aid (manufactured by Meisei Yakuhin Kogyo, K. K.). To examine metal allergic reactions on pure-metal elements used for dentistry, it is known to use such aqueous media of metal salts as set out in Table 1, given below.

TABLE 1

| No. | Metal | % | Base |
|---|---|---|---|
| 1 | $CuSO_4$ | 5 | Aq |
| 2 | $CuSO_4$ | 2 | Aq |
| 3 | $K_2Cr_2O_7$ | 0.4 | Aq |
| 4 | $NiSO_4$ | 5 | Aq |
| 5 | $NiSO_4$ | 2 | Aq |
| 6 | $CoCl_3$ | 2 | Aq |
| 7 | $HgCl_2$ | 0.1 | Aq |
| 8 | $HgCl_2$ | 0.05 | Aq |
| 9 | $SnCl_3$ | 2 | Aq |
| 10 | $SnCl_3$ | 1 | Aq |
| 11 | $CdSO_4$ | 1 | Aq |
| 12 | $HAuCl_4$ | 0.2 | Aq |
| 13 | $H_2PtCl_6$ | 0.5 | Aq |
| 14 | $PdCl_2$ | 1 | Aq |
| 15 | $FeCl_3$ | 2 | Aq |
| 16 | $SbCl_3$ | 2 | Pet. |
| 17 | $AgBr$ | 2 | Pet. |
| 18 | $ZnCl_2$ | 2 | Pet. |
| 19 | $MnCl_2$ | 2 | Pet. |

The aqueous media specified in Table 1 are all in the form of metal salts. The metal salts are placed on a pad in the form of one droplet, if liquefied, or a half grain of rice, if pasted, and the pad is applied on the back of a patient with the aid of Miniplaster (manufactured by Torii Yakuhin, K. K.).

In some cases, a dental Ni-Cr-Co alloy has been formed as such into a disc-like test piece of 4 mm in diameter and 1 mm in height, which has then been applied on a testing patch or a first-aid plaster to determine metal allergic reactions. However, this method is uncommon. That is, the function of the patch test plaster is only to apply a conventional test piece.

Heretofore, the metal allergic reactions have generally been examined by dissolving a metal for its ionization to form a metal salt solution and applying it onto gauze to make a determination of whether or not a living body becomes inflamed by allergic reactions.

However, the metals required for dental purposes are so particularly difficult to ionize that allergic reactions do not appear easily. With noble metals such as Au, Pt and others most commonly used as dental metals, such a tendency becomes especially marked. As an example, aqua regia or nitrohydrochloric acid capable of dissolving Au, Pt, etc. involves much difficulty in regulating it to around neutral pH of 7 to 8 due to its strong acidity. Results are also much different from those obtained with pure metals or metal alloys, once such dental metals are converted to their salts. In other words, the results often are useless, since the allergic reactions observed have taken place through the metal salts, not through the metals per se. Also, nonallergic inflammations due to pH values or salts are often mistaken for metal allergic inflammations. The dental metals are always used in the form of alloys except for rare occasions on which they are employed in their elemental state. Accordingly, it is likely that in the event that a certain pure metal, which is found to make no contribution to any allergic phenomenon, is alloyed with other metals, metal allergies may then be developed due to some synergistic effect resulting from such alloying.

The foregoing considerations imply that the examination of metal allergies by liquefying dental metals (alloys) into aqueous solutions of their salts tends to make erroneous judgements. In addition, the examination of allergic reactions on the individual metals isolated from an alloy is troublesome and, at the same time, is disadvantageous in that it is not possible to examine the metal allergic reaction of that alloy itself.

It is true that the method comprising forming a dental alloy itself into a disc-like test piece, by way of example, and applying it to the skin with the aid of a patch test plaster is simple to carry out, but it is difficult to ionize the alloy (or a metal) and convert it to a metal hapten by allowing it to contact the skin, unlike the metal salt, since it is through a complicated mechanism that the allergic reactions occur. Also, even though the metal hapten is formed, difficulty would be encountered in the event that it bonds especially to proteins in tissue fluids to form an organometallic compound which in turn becomes an antigen so sensitive to an individual as to produce an antibody. Especially, this holds for alloys of noble metals such as Au and Pt. Dentists should pay attention to the fact that in case a metallic prosthesis, especially if a metallic implant material is used without having a comprehensive understanding of the data of each patient about her or his metal allergies, the development of metal allergic reactions will bring results so harmful that inflammations, eruptions and erosions are spread to the mucous membranes i nthe mouth and, possibly, even to the whole system, thus resulting in chronic dermatitises which, reportedly, causes palmar and/or plantar pimples in particular. There is also the possibility that the bone may be absorbed or necrotized. It is thus essential and inevitable to make accurate determinations of the metal allergic reactions of a patch testing material for the purpose of preventing metallic allergies.

SUMMARY OF THE INVENTION

As a result of intensive studies made on a highly accurate and very simple patch testing material which eliminates the demerits of the conventionally available methods and materials for patch testing, the present inventors have successfully accomplished the present invention described hereinafter.

According to one aspect of the present invention, there is provided a patch test material for the detection of metal allergies, wherein a dental metal to be tested is allowed to be present together with an allergic reaction aid.

The other aspects and specific features of the present invention will become apparent from reading of the following detailed description with reference to the accompanying drawings, which are given by way of example along.

BRIEF DESCRIPTION OF THE DRAWINGS

FIG. 1 is a plan view showing one embodiment of the patch testing material according to the present invention, which will be explained in Example 1, FIG. 2 is an enlarged sectional view taken along the line A—A' of FIG. 1, FIG. 3 is a plan view showing another embodiment of the patch testing material according to the present invention, which will be explained in Example 2, FIG. 4 is an enlarged sectional view taken along the line B—B' of FIG. 3, FIG. 5 is a plan view illustrative of a conventionally available patch testing material, and FIG. 6 is an enlarged sectional view taken along the line C—C' of FIG. 5.

In the drawings:
a . . . adhesive tape
b . . . gauze
C . . . alloy powder
d . . . the immersion part of the solution containing L-cysteine
d' . . . the immersion part of the solution containing the Freund's incomplete adjuvant
e . . . small disc of the metal to be tested

DETAILED DESCRIPTION OF THE INVENTION

According to the patch test materials of the present invention, the dental metals per so to be tested in the form of a powder, a granular or a rounded small disc are allowed to be present along with a high molecular weight compound acting as an allergic reaction aid, which, among others, includes proteins, glycoproteins, Freund's incomplete adjuvant and especially the Sh type group of proteins. Of the high molecular weight compounds as mentioned above, particularly effective are L-cysteine, L-methionine, L-glutamine, L-glutamic acid and L-leucine and so on selected from essential amino acids, but the present invention is not limited thereto.

It is understood that proteins are a general name of a group of high-molecular, nitrogen-containing organic materials contained as the main component in the cells of what is generally called organisms inclusive of animals, vegetables and microbes. The proteins comprise a polypeptide chain ($H_2N-CHR_1-CO-NH-CHR_2-CO-NH-CHR_3-CO$ . . . ) consisting of recurring units of various L-alpha-amino acids ($H_2N-CHR-COOH$, including glycine of R=H) through peptide bonds ( . . . $-CO-NH-$ . . . ). Naturally occurring proteins producing amino acids along by hydrolysis are called the simple proteins, and proteins producing amino acids as well as other organic matters, the composite proteins. The former proteins are referred to as albumin, globulin, prolamin, gluten, scleroprotein, histone, protamine and the like, and the latter, nucleoprotein, glycoprotein, lipoprotein and the like. Besides, there are a group of the so-called derived proteins inclusive of gelatin and peptone, which do not belong to natural proteins but are derivable from slightly varied natural proteins.

By strict definition in chemical terms, glycoproteins stand for a group of proteins having a heterosaccharide side chain covalently bonded to a specific amino acid residue of their polypeptide chain. The polypeptide chain has an amino acid sequence inherent in each molecule, and the saccharide chain is glycocide-bonded to any one of the hydroxide residues of serine or threonine, the acid amide residue of asparaginic acid and the hydroxide residue of oxylysine. The glycoproteins do not only form main constituents of extracelluar secretive proteins such as plasma (47 types inclusive of albumin), egg white (ovomucoid) and milk (γ-casein), but also include fibrous proteins such as collagen and hormones such as gonadotropin. These proteins and glycoproteins are also found to be effective in the present invention.

The metals to be used may be employed in the form of a powder, a granule or a rounded small metal disc, and refer to every metal which has been used or may potentially be used in dental fields. Generally, currently used dental alloys have their primary object to prepare dental restoratives, are of diversity and versatility enough to meet a variety of demands, and are by and large broken down into the following categories:

(1) Noble Metal Alloys

Gold-Base Alloys
- Gold Foils (Pure Gold)
- Casting Gold Alloys
  - Types I to IV
  - Alloys per karat
- Wrought Gold Alloys
- Gold Alloys for metal bonding procelain Silver-Base Alloys
- Low-fusing Silver Alloys (Ag—Sn—Zn)
- Gold—Silver—Palladium Alloys (Ag—Cu—Pd—Au)
- Amalgam Alloys (Ag—Sn)

(2) Base Metal Alloys

Nickel Chromium Alloys
- Casting Nickel—Chromium Alloys
- Wrought Nickel—Chromium Alloys
- Nickel—Chromium Alloys for metal bonding porcelain Cobalt—Chromium Alloys
Cobalt—Chromium—Nickel Alloys
Iron—Base Alloy (stainless steel)

The aforesaid dental alloys are used in the form of a powder, a granule or a rounded small metal disc. The patch test materials of the present invention may contain the allergic reaction aids and the dental alloy or pure metals, and may further include an aqueous solution of a water-soluble high-molecular weight compound functioning as an adhesive or thickening material. The water-soluble high-molecular weight compound used may include natural ones such as starches (based on sweet potatoes, potatoes, tapioca and the like), marine plants (such as funorin, agar and sodium alginate and the like), viscous matters of vegetable origin (such as yams, gum tragacanth and gum arabic and the like) and proteins (such as glue, gelatin, casein and collagen and the like); and semi-synthetic ones based on celluloses (such as methyl cellulose, ethyl cellulose, hydroxyethyl cellulose and carboxymethyl cellulose and the like) and starches (soluble starch and carboxymethyl starch and the like); and synthetic ones (such as polyvinyl alcohol, sodium polyacrylate and polyethylene oxide and the like).

Referring in further detail to the patch test material of the present invention, a pure metal or a metal alloy present in the patch test material functions to make a chemical, particularly, chelate bond to the allergic reaction aid also present therein, thereby forming a metal hapten which is easily taken in a living body. It is thus possible to eliminate the disadvantages of the conventional patch testing wherein metal salts are prepared and used as the materials therefor.

The disadvantages of the conventional patch test using metal salts are:

(1) Since it is impossible to dissolve the metal alloy to be used in an identical electrolyte for its ionization to obtain the individual metal salts, it is impossible to make a determination of what metal allergies result from the individual metal elements forming such a metal alloy.

(2) A great deal of labor is needed to isolate the metal alloy to be used into the individual metals and form the corresponding salts.

(3) When the metal salts are used, inflammations caused by reactions other than metal allergies, which vary depending upon the type of the salts and pH values, are indistinguishable from those brought about by metal allergies.

The disadvantages of another conventional patch test wherein the dental alloys formed into a disc-like test piece are applied as such to a suitable site with the aid of a patch testing plaster can also be eliminated.

The disadvantages of the conventional patch test making use of the dental alloys formed into a disc-like test piece are that:

(1) When the metal to develop metal allergic reactions is contained in a smaller amount, its direct chemical bonding to a living body is so difficult that a metal hapten is hard to form.

(2) A noble metal alloy having particularly high contents of Au and Pt make a direct chemical, particularly, chelate bond to a living body, making it difficult to form a metal hapten.

The patch test materials of the present invention successfully overcome the demerits of the conventional patch test, and are designed such as to allow the pure metals or alloys present therein to first form a chemical, particularly, a chelate bond to the allergic reaction aid also present therein to form a metal hapten which is easily taken in a living body. Thus, the present patch test materials improve the accuracy to metal allergic reactions, and are easier to handle.

The patch test materials according to the present invention are applicable not only to the dental field but to their fields as well, wherein metal alergies may potentially be developed through the contact of pure metals or metal alloys with the human body. For instance, the present materials may find use in fields of prosthesis, medical man-made joints or bones, metals, screws and wires for the fixation of broken bones, metallic conduits and acupuncturation/moxibustion. It is appreciated that the present testing materials may take on various forms, if only they contain the prescribed allergic reaction aids and pure metals or metal alloys. For instance, the allergic reaction aids may be dissolved in a large amount of water with or without a water-soluble high molecular weight compound to form a solution which has a liquid or pasty appearance, and the pure metals or metal alloys in the form of a powder, a granule or a rounded small metal disc may be allowed to be present therein. Alternatively, the present materials may be placed on gauze attached to a patch test plaster for service.

EXAMPLES

The patch test materials of the present invention will now be explained in further detail with reference to the following nonrestrictive examples.

EXAMPLE 1

A patch test material was prepared in the manner as described below. First, L-cysteine was diluted with physiological saline to a concentration of $5.0 \times 10^{-2}$ mol/l, and was added with 0.5% of sodium polyacrylate. The resulting solution was then regulated to pH 7 with calcium carbonate, and was made viscous. A powdery alloy of Ag-Sn-Cu (having an average particle diameter of 20 μm and manufactured by G-C Dental Industrial Corp.) and available under the trade name of Lumialloy was added with stirring to the resulting solution in such a manner that it accounted for 30% by weight of the whole solution. Three droplets of the thus obtained product was added to gauze, on the back side of which a sensitivity testing tape (manufactured by 3M, Co., Ltd.) available under the trade name of Incize Drape was placed under pressure, thereby preparing the patch test material according to the present invention.

EXAMPLE 2

In place of L-cysteine, a Freund's incomplete adjuvant was diluted with physiological saline to a concentration of $3.0 \times 10^{-2}$ mol/l in a similar manner as described in Ex. 1. Added to the resulting solution were sodium polyacrylate and calcium carbonate in the same amounts as used in Example 1. Three droplets of the thus obtained product were added on gauze, on which a rounded small disc of the metal to be tested, 3 mm in diameter and 1 mm in thickness, was placed, and on the other side of which the sensitivity testing tape described above was placed under pressure, thereby preparing the patch test material according to the present invention.

COMPARATIVE EXAMPLE 1

For the purpose of comparing with the powdery alloy of Ag-Sn-Cu, the individual metal salts were prepared to make a patch test material. As a replacement to Ag, AgBr was dispersed in vaseline to prepare a 2% pasty product. As a replacement to Sn, $SnCl_3$ was dissolved in distilled water to prepare a 2% solution. As a replacement to Cu, $CuSO_4$ was dissolved in distilled water to prepare a 2% solution. About three droplets of each solution were added on gauze, on the back side of which the sensitivity testing used in the foregoing tests, was placed under pressure, thereby preparing three patch testing materials.

COMPARATIVE EXAMPLE 2

Five (5.0) % sodium polyacrylate was added to physiological saline, and the resulting solution was regulated to pH 7 with the addition of calcium carbonate, and was made viscous. A powdery alloy of Ag—Sn—Cu (having an average particle diameter of 20 μm and manufactured by G-C Dental Industrial Corp.) available under the trade name of Lumialloy was added with stirring to the resulting solution in such a manner that it accounted for 30% by weight of the whole solution. Three droplets of the thus obtained product was added to gauze, on the back side of which the same tape as sensitivity testing tape used earlier, was placed under pressure, thereby preparing the patch test material.

In the patch test material of Example 1, the powdery alloy was present together with, i.e., colloidally and uniformly dispersed in, a solution of L-cysteine, one component of the present patch test material and a high molecular weight compound for the purpose of increasing the viscosity thereof and preventing the evaporation of moisture therefrom, and the dispersed solution was placed on gauze which was then applied with an adhesive tape. In the patch test material of Example 2, the solution containing the Freund's adjuvant, one component of the patch testing material according to the present invention and a high molecular weight compound was increased in viscosity and prevented from giving out moisture, and was placed on gauze on which a small disc of the metal to be tested was placed, and on the other side of which an adhesive tape was applied.

In Comparative Example 1 illustrative of the conventional patch testing, the alloy used in Example 1 was broken down into the consititutional metal elements from which the corresponding salts were formed. Each salt was then placed on gauze which was applied to an adhesive tape, thereby preparing the patch test materials. To prepare the patch test materials of Comparative Example 1, it is required to examine the composition of the alloy to be used, and it is not easy to form the corresponding salts of the individual metal elements. Unlike Examples 1 and 2, it is not possible to make determinations of the metal allergies of the metal per se to be used.

As a result of patch testing carried out with the patch test material obtained in Example 1, metal allergic reactions are clearly found. When the patch test materials obtained in Comparative Example 1 were used, however, metal allergic reactions took place through the metal salts, not due to the presence of metals to be examined, so that any metal allergic reactions inherent in the metals to be examined could not be observed. This implies that the metal allergic reactions occurred through pH values or the metal salts so that they were hardly distinguishable from the inherent metal allergic reactions, indicating that the conventional determination with metal salts is of less accuracy. In Example 2, metal allergic reactions were clearly found. In Comparative Example 2, however, any reaction with a living body was not observed whatsoever.

EFFECT OF THE INVENTION

According to the patch testing materials of the present invention, the pure metals or metal alloys to be used are made integral with the allergic reaction aids, i.e., high molecular weight compounds such as proteins or Freund's emulsion through a chemical, particularly, chelate bond to form a metal hapten which is easily taken in a living body. With the present materials, it is thus possible to attain breakthroughs such as improvements in the accuracy of determinations of metal allergic reactions and prevention of metal allergies in a simple manner.

What is claimed is:

1. In a patch test material for the detection of metal allergies, the improvement which comprises the presence, therein, of a dental metal or an alloy thereof and a biological high molecular weight compound as an allergic reaction aid.

2. A patch test material as claimed in claim 1, wherein the allergic reaction aid is a protein.

3. A patch test material as claimed in claim 1, wherein the allergic reaction aid is a Freund's incomplete adjuvant.

4. A patch test material as claimed in any one of claims 1, 2 and 3, wherein the dental metal is a noble metal.

5. A patch test material as claimed in any one of claims 1, 2 and 3, wherein the dental metal is a base metal.

* * * * *